United States Patent [19]

Coates

[11] 4,252,119

[45] Feb. 24, 1981

[54] PACK FOR MOIST PATIENT THERAPY

[75] Inventor: John T. Coates, Hoffman Estates, Ill.

[73] Assignee: The Kendall Company, Boston, Mass.

[21] Appl. No.: 48,215

[22] Filed: Jun. 13, 1979

[51] Int. Cl.³ .............................................. A61F 7/02
[52] U.S. Cl. .................................................. 128/268
[58] Field of Search ................................ 128/155–156, 128/260–261, 268; 206/438, 441

[56] References Cited

U.S. PATENT DOCUMENTS

| | | | |
|---|---|---|---|
| 2,840,080 | 6/1958 | Clark | 128/260 |
| 2,999,265 | 9/1961 | Duane et al. | 128/260 |
| 3,416,522 | 12/1968 | Yeremian | 128/268 |
| 3,421,502 | 1/1969 | St. Clair | 128/268 |
| 3,657,760 | 4/1972 | Kudisch | 128/268 |
| 3,685,645 | 8/1972 | Kawaguchi | 206/438 |
| 3,709,221 | 1/1973 | Riely | 128/156 |
| 3,777,754 | 12/1973 | Plachy | 128/268 |

FOREIGN PATENT DOCUMENTS

| | | | |
|---|---|---|---|
| 85032 | 4/1965 | France | 128/268 |
| 349749 | 12/1960 | Switzerland | 128/268 |

Primary Examiner—Robert W. Michell
Assistant Examiner—C. F. Rosenbaum
Attorney, Agent, or Firm—Powell L. Sprunger

[57] ABSTRACT

A pack for moist patient therapy comprising, a wet dressing having an absorbent layer for placement toward a patient, and a backing sheet of liquid impervious material covering a back surface of the layer. The pack has an envelope of liquid and bacteria impervious material defining a closed cavity, with the dressing being received in the cavity. The pack also has a sterile liquid received in the cavity in sufficient volume to impregnate the absorbent layer of the dressing.

10 Claims, 8 Drawing Figures

PACK FOR MOIST PATIENT THERAPY

BACKGROUND OF THE INVENTION

The present invention relates to packs for moist patient therapy.

In the past, wet dressings have been heated and used in moist heat therapy for a number of patient afflictions. Prior wet dressings normally comprise a foil package which retains a multi-ply gauze sheet inpregnated with a sterile liquid. The packages are heated in a suitable manner for a period of time, such as beneath a heat lamp, after which the gauze is removed from the package and applied in heated form to the patient. The conditions for which heated wet dressings may be used in moist heat therapy include the following: (a) localized tissue infections, such as boils, carbuncles, eye inflammation, lymphangitis, and phlebitis; (b) ulcerations, such as decubitus ulcers, skin ulcers, and venous ulcers; (c) surgical wounds, such as infected suture wounds, hemorrhoidectomy, and pilonidal cysts; (d) traumatized tissue, such as lacerations, contusions, and accidental amputations; and (e) dermatological conditions, such as contact dermatitis, and psoriasis. Also, the wet dressings may be refrigerated and used as a cold compress for special conditions, such as to relieve swelling, inflammation, pain, and bleeding due to injuries.

SUMMARY OF THE INVENTION

A principal feature of the present invention is an improved pack for moist patient therapy.

The pack of the invention comprises a wet dressing having absorbent layer means for placement toward a patient, and a backing sheet of liquid impervious material covering a back surface of the layer means. The pack has an envelope of liquid and bacteria impervious material defining a closed cavity, with the dressing being received in the cavity. The pack also has a sterile liquid received in the cavity in sufficient volume to impregnate the absorbent layer means of the dressing.

A feature of the present invention is that when the pack is heated the liquid evaporates from the outside of the backing sheet, and permits removal of the dressing from the envelope by contacting the dry backing sheet without wetting the hands.

Thus, a feature of the invention is that the dressing of the present invention is more convenient for application to the patient by hospital personnel.

A further feature of the invention is that the bacteria impervious backing sheet is contacted by the hands, rather than the moist absorbent portion of the dressing, during placement on the patient to minimize the possibility of contamination of the dressing.

Another feature of the invention is that when the heated dressing is applied to the patient, the backing sheet insulates the dressing and maintains the dressing in a heated condition for longer periods of time.

Yet another feature of the invention is that the backing sheet retards evaporation and reduces moisture loss from the absorbent layer means during use of the dressing.

Further features will become more fully apparent in the following description of the embodiments of this invention and from the appended claims.

DESCRIPTION OF THE PREFERRED EMBODIMENTS

Figure 1:
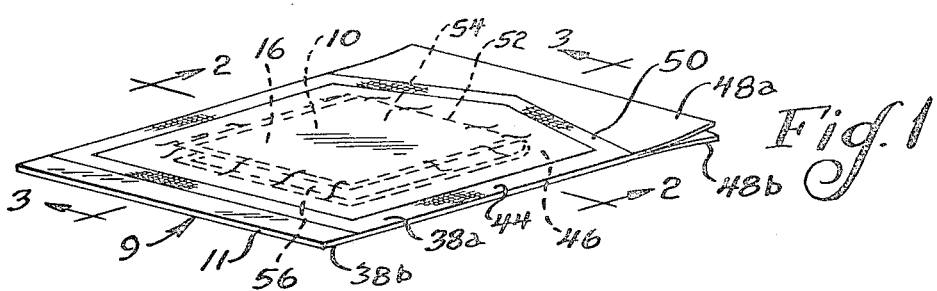
FIG. 1 is a perspective view of a moist therapy pack of the present invention.
Figure 2:
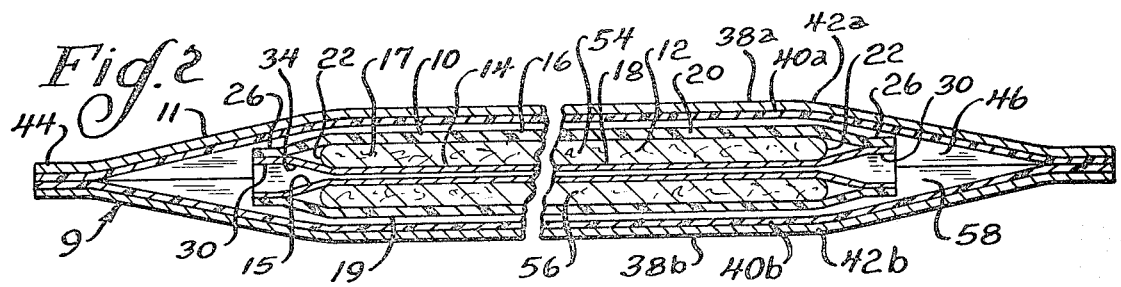
FIG. 2 is a fragmentary sectional view taken substantially as indicated along the line 2—2 of FIG. 1.
Figure 3:
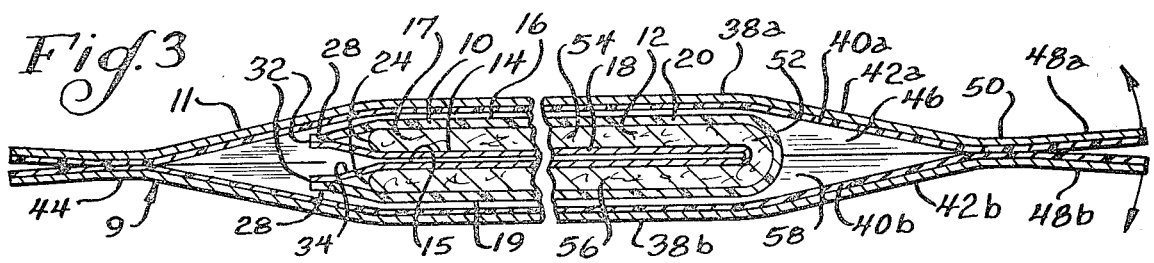
FIG. 3 is a fragmentary sectional view taken substantially as indicated along the line 3—3 of FIG. 1.
Figures 5, 6:
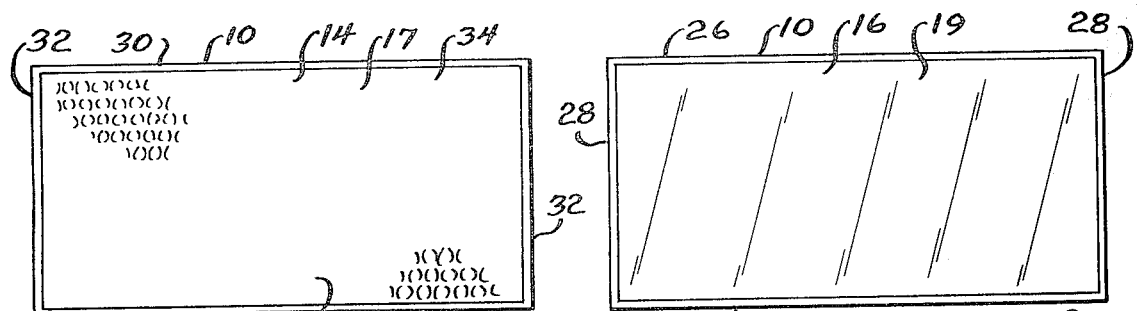
FIG. 5 is a front plan view of the dressing.
FIG. 6 is a back plan view of the dressing.

Referring now to FIGS. 1-3, 5, and 6, there is shown a pack 9 for moist patient therapy having a wet dressing 10 and an envelope or package 11 for covering the dressing 10. The dressing 10 has an absorbent pad 12, a liquid pervious top or cover sheet 14 defining a front surface 15 of the dressing 10, and a liquid and bacteria impervious backing sheet 16 defining a back surface 19 of the dressing 10, with the pad 12 and cover sheet 14 defining absorbent layer means 17 for the dressing 10. The pad 12 has a front surface 18, a back surface 20, a pair of side edges 22, and a pair of end edges 24 connecting the side edges 22. The pad 12 may be constructed from any suitable material, such as a mass of cellulosic fibers loosely formed by comminuting wood pulp, termed in the art as wood fluff, or a plurality of sheets of absorbent tissue or absorbent nonwoven material.

The backing sheet 16 covers the back surface 20 of the pad 12, and extends the length and width of the pad. As shown, the backing sheet 16 has side and end margins 26 and 28, respectively, which are joined to side and end margins 30 and 32, respectively, of the top sheet 14 by any suitable means, such as adhesive or RF sealing of the backing sheet 16 to the top sheet 14, with the sealed margins extending peripherally around the pad 12 which is located intermediate the top and backing sheets 14 and 16. The top sheet 14 may be made of any suitable material, such as a nonwoven material, and, in a preferred form, the front surface 15 defined by the top sheet is nonadherent to the wound of a patient. In a suitable form, the top sheet 14 may be made of a polyester-rayon nonwoven material, such as micrexed Novonette ® SP117, a trademark of The Kendall Company, Boston, Massachusetts.

The backing sheet 16 may be made from a suitable material which is impervious to passage of liquids and bacteria, but which preferably is pervious to passage of gas and water vapor. In a suitable form, the backing sheet 16 may be constructed from a polyether based thermoplastic polyurethane film, such as Tuftane 410, a trademark of B. F. Goodrich General Products Company, Akron, Ohio, with a thickness in the range of approximately 0.4 to 1.4 mils. Such a film with a 1.0 mil thickness provides an absolute bacterial barrier and has the following moisture vapor transmission and gas transmission characteristics:

Moisture Vapor Transmission
(gms./24 hr.-100 sq. in.)

-continued

| 70 |
| --- |
| Gas Transmission Rate (cc/24 hr.-100 sq. in.-ATM) |

| Oxygen | 1,000 |
| --- | --- |
| Nitrogen | 450 |
| Carbon Dioxide | 4,300 |

Also, such a material is resistant to melting at the normal temperatures used during steam sterilization of about 250° F., and is believed to melt in the range of about 350°–400° F., such that the dressing may be subjected to steam sterilization without deleteriously affecting the backing sheet, as well as the lower temperatures of about 115°–120° F. used to heat the pad immediately prior to use of the wet dressing. Where desired, the backing sheet may be sealed in the dressing through use of relatively high temperatures, or by RF sealing, as previously discussed. Possible alternative materials which might be utilized for the backing sheets are silicone, a polyester based thermoplastic polyurethane film, microporous polytetrafluoroethylene, a material sold under the trademark Gore-Tex by W. L. Gore & Associates of Newark, Delaware. Some materials which appear to be possible candidates for such a backing sheet are undesirable for this purpose, since such materials melt at relatively low temperatures, and the dressing could not be subjected to steam sterilization without destruction of the backing sheet and dressing.

The envelope 11 comprises first and second opposed sheets 38a and 38b, with the sheets 38a and b comprising an inner sealable layer 40a and 40b, such as a thermoplastic material, and an associated outer layer 42a and 42b of a heat resistant (relative to sterilization temperatures), heat conductive, liquid and bacteria impervious material, such as aluminum foil, with the layers 40a and 42a of sheet 38a and the layers 40b and 42b of sheet 38b being laminated together. As shown, the sheets 38a and b are sealed together, such as by heat or RF sealing, along a peripheral seal line 44 joining the sheets 38a and b together and defining a closed cavity 46 intermediate the sheets 38a and b. As shown, the sealed envelope 11 has a pair of opposed end flaps 48a and b defined by end portions of the sealed sheets 38a and b extending from a laterally extending end portion 50 of the seal line 44, such that the flaps 48a and b may be grasped and pulled to rupture the seal line 44 from a location in the end portion 50 of the seal line 44.

As shown, the dressing 10 has a laterally extending central fold line 52 defining opposed end sections 54 and 56 of the dressing 10 of approximately equal length, with the end sections 54 and 56 being folded against each other in a configuration with the backing sheet 16 facing outwardly from the folded dressing 10. The folded dressing 10 is received in the envelope cavity 46 in a configuration with the fold line 52 facing toward the end seal portion 50 for a purpose which will be described below. The pack 9 has a sterile liquid 58, such as distilled water or a saline solution, received in the envelope cavity 46 in sufficient volume to impregnate and wet the absorbent layer means 17 of the dressing 10. After assembly, the pack 9 is subjected to sterilization, such as heat sterilization, in order to render the wet dressing 10 sterile, with the sheets 38a and b of the envelope 11 maintaining the dressing 10 in a sterile condition until use.

Figure 4:
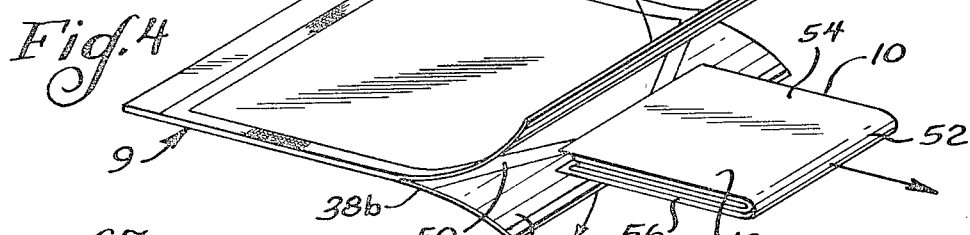
FIG. 4 is a perspective view illustrating removal of a wet dressing from an envelope of the pack of FIG. 1.

In use, the pack 9 is placed in the presence of a heat source, such as heat lamp, in order to heat the dressing 10 in the closed envelope 11, with the foil layers 42a and b of the envelope conducting heat from the heat source to the dressing 10. In suitable form, the dressing 10 may be heated to approximately 115°–120° F., as previously discussed. During heating, the liquid 58 evaporates from the back surface 19 of the backing sheet 16 while the heated absorbent layer means 17 remains in a wetted condition. After the pack 9 has been heated for a sufficient length of time, e.g., 2–3 minutes, the flaps 48a and b of the envelope 11 are utilized to rupture the seal line 44 adjacent the end seal portion 50 to expose the dressing 10 adjacent the fold line 52, as shown in FIG. 4. Next, the dressing 10 may be grasped by the fingers on the back surface 19 of the backing sheet 16 adjacent the fold line 52, and may be removed from the envelope 11 while the dry backing sheet 16 prevents wetting of the user's hands and minimizes possibility of contamination to the wetted and heated absorbent layer means 17. The dressing 10 may then be unfolded and applied to the patient in the heated condition with the absorbent layer means 17 facing toward the patient. In this configuration, the backing sheet 16 serves to insulate the heated absorbent layer means 17 to reduce heat loss and maintain the dressing 10 in a heated condition for longer periods of time. Also, although the backing sheet 16 may be somewhat pervious to moisture vapor, it retards evaporation from the absorbent layer means 17, and reduces liquid loss during use of the dressing.

Figures 7, 8:
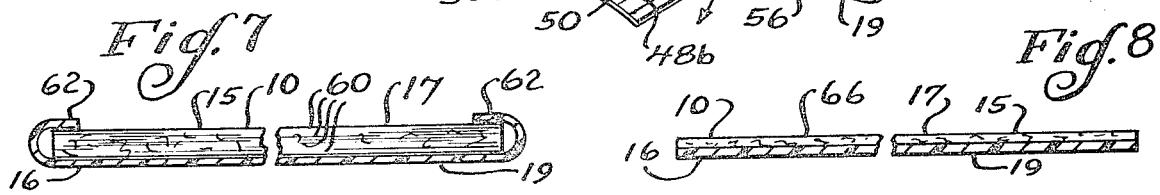
FIG. 7 is a fragmentary sectional view of another embodiment of a wet dressing for the pack of the present invention.
FIG. 8 is a fragmentary sectional view of another embodiment of a wet dressing for the pack of the present invention.

Another embodiment of the wet dressing for the pack of the present invention is illustrated in FIG. 7, in which like reference numerals designate like parts. In this embodiment, the absorbent layer means 17 comprises a plurality of sheets 60 of an absorbent material, such as a suitable tissue or absorbent nonwoven material, e.g., the micrexed nonwoven material described for the cover sheet 14 in connection with the embodiment of FIGS. 1–6. As shown, the liquid impervious backing sheet 16 may have lateral side margins 62 folded over and secured to a front surface of the absorbent layer means 17 by suitable means, such as adhesive. The wet dressing 10 of FIG. 7 may be folded and placed in the envelope cavity, and is impregnated with a sterile liquid, as previously described in connection with FIGS. 1–6.

Another embodiment of the wet dressing for the pack of the present invention is illustrated in FIG. 8, in which like reference numerals designate like parts. In this embodiment, the absorbent layer means 17 comprises a sheet 66 of absorbent material, such as a tissue or absorbent nonwoven material, e.g., the micrexed nonwoven material described for the cover sheet 14 of the dressing of FIGS. 1–6. The absorbent sheet 66 may be laminated to the liquid impervious backing sheet 16 in any suitable manner, and the dressing may be folded and placed in the envelope cavity in a liquid impregnated condition, as previously discussed in connection with FIGS. 1–6. The backing sheet 16 in the embodiment of FIGS. 7 and 8 may be constructed of the materials discussed for the backing sheet in the embodiment of FIGS. 1–6.

The foregoing detailed description is given for clearness of understanding only, and no unnecessary limitations should be understood therefrom, as modifications will be obvious to those skilled in the art.

I claim:

1. A pack for moist patient therapy, comprising:
a wet dressing having absorbent layer means for placement toward a patient, and a backing sheet of liquid and bacteria impervious material covering a back surface of the layer means, the material of said backing sheet being resistant to heat under normal sterilization temperatures;

an envelope of liquid and bacteria impervious material defining a closed cavity, with the material of said envelope being heat conductive and resistant to heat at normal sterilization temperatures, with said dressing being folded along a lateral central fold line defining first and second end sections of approximately equal length, and with the dressing received in said cavity with said backing sheet facing outwardly from the folded dressing; and a sterile liquid received in said cavity in a sufficient volume to impregnate the absorbent layer means of the dressing.

2. The pack of claim 1 wherein said envelope includes rupturable sealing means for initially opening the envelope, and in which said fold line faces toward said sealing means.

3. The pack of claim 1 wherein said backing sheet comprises a material pervious to passage of water vapor and gas.

4. The pack of claim 1 wherein said backing sheet comprises a polyether based thermoplastic polyurethane film.

5. The pack of claim 1 wherein said envelope comprises aluminum foil.

6. The pack of claim 1 wherein said layer means comprises a fluid pervious cover sheet, and an absorbent pad located intermediate said cover and backing sheets.

7. The pack of claim 1 wherein said layer means comprises at least one sheet of an absorbent material.

8. The pack of claim 7 wherein said sheet comprises a nonwoven material.

9. The pack of claim 7 wherein said layer means comprises a plurality of superimposed sheets of absorbent material.

10. The pack of claim 1 wherein said layer means comprises a sheet of absorbent material laminated to said backing sheet.

* * * * *